US011389671B2

United States Patent
Aono (10) Patent No.: US 11,389,671 B2
(45) Date of Patent: Jul. 19, 2022

(54) PARTICLE BEAM TREATMENT SYSTEM AND METHOD FOR RENEWING FACILITIES OF PARTICLE BEAM TREATMENT SYSTEM

(71) Applicant: Hitachi, Ltd., Tokyo (JP)

(72) Inventor: Hidehiro Aono, Tokyo (JP)

(73) Assignee: HITACHI, LTD., Tokyo (JP)

( * ) Notice: Subject to any disclaimer, the term of this patent is extended or adjusted under 35 U.S.C. 154(b) by 19 days.

(21) Appl. No.: 16/217,089

(22) Filed: Dec. 12, 2018

(65) Prior Publication Data
US 2019/0269941 A1    Sep. 5, 2019

(30) Foreign Application Priority Data
Mar. 2, 2018    (JP) .............................. JP2018-037516

(51) Int. Cl.
*A61N 5/10* (2006.01)
*H05H 7/00* (2006.01)
*H05H 13/04* (2006.01)

(52) U.S. Cl.
CPC ......... *A61N 5/1077* (2013.01); *A61N 5/1065* (2013.01); *A61N 5/1075* (2013.01); *A61N 5/1079* (2013.01); *A61N 5/1042* (2013.01); *A61N 2005/1087* (2013.01); *H05H 7/001* (2013.01); *H05H 13/04* (2013.01); *H05H 2277/11* (2013.01)

(58) Field of Classification Search
None
See application file for complete search history.

(56) References Cited

U.S. PATENT DOCUMENTS

| 6,683,318 B1 * | 1/2004 | Haberer | A61N 5/10 250/492.3 |
| 2004/0118081 A1 * | 6/2004 | Reimoser | A61N 5/1079 52/749.1 |

(Continued)

FOREIGN PATENT DOCUMENTS

| EP | 0 869 199 A1 | 10/1998 | |
| JP | H0211764 B2 * | 3/1990 | A47C 4/40 |

(Continued)

OTHER PUBLICATIONS

Extended European Search Report received in corresponding European Application No. 18213303.3 dated Jul. 26, 2019.

(Continued)

*Primary Examiner* — James Choi
(74) *Attorney, Agent, or Firm* — Mattingly & Malur, PC (57) ABSTRACT

To provide a particle beam treatment system and a method for renewing facilities of the particle beam treatment system with which the facilities can be renewed efficiently. A particle beam treatment system 1 includes a charged particle beam generation device 2 that generates a charged particle beam Bm, a first irradiation device 4(1) that irradiates the charged particle beam to a predetermined irradiation target, a first beam transportation device 3(1) that transports the charged particle beam from the charged particle beam generation device 2 to the first irradiation device 4(1), and a first vacuum valve 33(1) that is arranged in the first beam transportation device 3(1).

10 Claims, 8 Drawing Sheets

(56) References Cited

U.S. PATENT DOCUMENTS

| | | | |
|---|---|---|---|
| 2012/0119106 A1* | 5/2012 | Uno | A61N 5/1077 |
| | | | 250/396 ML |
| 2013/0228698 A1 | 9/2013 | Kakutani et al. | |
| 2014/0088336 A1* | 3/2014 | Hagino | A61N 5/1081 |
| | | | 600/1 |
| 2014/0296610 A1 | 10/2014 | Nishiuchi | |

FOREIGN PATENT DOCUMENTS

| | | | | |
|---|---|---|---|---|
| JP | 5-62606 A | | 3/1993 | |
| JP | 2000075100 A | * | 3/2000 | ........... A61N 5/1079 |
| JP | 2007-95553 A | | 4/2007 | |
| JP | 2007268031 A | * | 10/2007 | |
| JP | 2012-100915 A | | 5/2012 | |
| JP | 5409521 B2 | | 2/2014 | |
| JP | WO2013/011583 A1 | | 2/2015 | |

OTHER PUBLICATIONS

Japanese Office Action received in corresponding Japanese Application No. 2018-037516 dated Apr. 20, 2021.
Japanese Office Action received in corresponding Japanese Application No. 2018-037516 dated Jul. 6, 2021.

\* cited by examiner

PARTICLE BEAM TREATMENT SYSTEM AND METHOD FOR RENEWING FACILITIES OF PARTICLE BEAM TREATMENT SYSTEM

CROSS-REFERENCE TO RELATED APPLICATION

The present application claims priority from Japanese application JP 2018-037516, filed on Mar. 2, 2018, the contents of which is hereby incorporated by reference into this application.

TECHNICAL FIELD

The present invention relates to a particle beam treatment system and a method for renewing facilities of the particle beam treatment system.

BACKGROUND ART

A particle beam treatment system is known which executes treatment by irradiating a charged particle beam of protons, or heavy ions, and the like to a diseased part (Patent Literature 1).

CITATION LIST

Patent Literature

Patent Literature 1: Japanese Patent No. 5409521
Patent Literature 2: U.S. Patent Application Laid-Open No. 2014/0296610

SUMMARY OF INVENTION

Technical Problem

For example, when an existing particle beam treatment system has been dilapidated or when the number of patients of the target of treatment by the particle beam has increased, it is necessary to add a new irradiation device to the existing system. However, in this case, it is expected that a significant stop time of the apparatus is required until completion of a series of works such as the construction for addition, adjustment, and testing of the new irradiation device.

Similarly, such case is also possible that an old irradiation device included in the existing system is replaced by a new irradiation device to which a new technology is applied. In this case also, it is expected that a long stop time of the apparatus is required until completion of a series of works.

While a series of works of them are executed, vacuum inside the existing system cannot be kept. Thereby, because the charged particle beam could not be accelerated/transported, during the working period, the existing system could not be operated for a long period, and treatment could not be executed. When the configuration of the existing particle beam treatment system is to be renewed, if the time until the renewal is completed and the particle beam treatment system restarts is long, the income of treatment expected during operation of the particle beam treatment system cannot be anticipated, and the financial burden of management of an apparatus provider increases.

The aim of the present invention is to provide a particle beam treatment system and a method for renewing facilities of the particle beam treatment system with which the facilities can be added and renewed efficiently.

Solution to Problems

In order to solve the problems described above, a particle beam treatment system according to the present invention includes a charged particle beam generation device that generates a charged particle beam, a first irradiation device that irradiates the charged particle beam to a predetermined irradiation target, a first beam transportation device that transports the charged particle beam from the charged particle beam generation device to the first irradiation device, and a first vacuum valve that is arranged in the first beam transportation device.

Advantageous Effects of Invention

According to the present invention, by closing the first vacuum valve, the facilities can be added or renewed while keeping the degree of vacuum on the route from the first vacuum valve to the charged particle beam generation device, the time for stopping the charged particle beam generation device can be shortened, the income of treatment during the period of adding or renewing the facilities can be anticipated, and the financial burden of an apparatus provider can be reduced.

DESCRIPTION OF EMBODIMENTS

Below, embodiments of the present invention will be explained based on the drawings. As described below, the particle beam treatment system related to the present embodiment has a configuration in which expandability is considered beforehand. Thereby, according to the present embodiment, the renewal work (partial replacement of the existing facility, addition of the new facility) can be executed within a short period.

In the present embodiment, on the boundary of the renewal object region and the region other than that (nonrenewed region; maintained region), a vacuum valve for keeping the degree of vacuum is arranged. As described above, the renewal object region can be separated into that of a case where a new facility is added and that of a case where a part of the existing facility is replaced (changed).

When a new facility is added, a vacuum valve is installed beforehand on the boundary of the region where addition of the new facility is planned and the existing facility (almost all becomes the maintained region). By keeping the vacuum valve closed, the vacuum state of the existing facility can be kept. Also, while keeping the vacuum state of the existing facility, the new facility is connected to a point beyond the vacuum valve, and required work is executed. Because the new facility and the existing facility are separated from each other by the vacuum valve, the impact of the installation work and the connection work of the new facility on the existing facility can be suppressed. Thereby, the new facility can be installed beyond the vacuum valve within a comparatively short period while continuing operation (running) of the existing facility.

By sucking the new facility by a vacuum pump after completion of installation of the new facility, the degree of vacuum of the new facility is made to agree to the degree of vacuum of the existing facility. By opening the vacuum valve after agreement of the degree of vacuum of the new facility and the degree of vacuum of the existing facility, the new facility and the existing facility are connected to each other physically (in terms of a flow of the charged particle beam). By arranging a vacuum valve beforehand also in the new facility added, addition of a still new facility can be coped with.

Also, the control device of the new facility and the control device of the existing facility may be configured so as to be separated from each other and to cooperate with each other, and the existing control device may be replaced by a new control device.

When a part of the existing facility is to be replaced, a vacuum valve is arranged beforehand on the boundary of the region of the replacement object (the apparatus of the replacement object out of the existing facility) and the region other than that (the apparatus left as it is out of the existing facility; the apparatus of the maintained region). By keeping the vacuum valve open, operation of the existing facility can be continued as usual.

Also, the vacuum valve is closed before attaching the new facility, and the new facility and the existing facility (the maintained region) are separated from each other. In a state separation has been completed, the new facility is installed beyond the vacuum valve. The new facility installed beyond the vacuum valve is sucked by the vacuum pump, and the degree of vacuum of the new facility is made to agree to the degree of vacuum of the existing facility that is separated by the vacuum valve. After agreement of the degree of vacuum of the new facility and the degree of vacuum of the existing facility that is used continuously as it is, the vacuum valve is opened again. Thereby, a part of the existing facility can be replaced by the new facility within a comparatively short period.

As described below, the particle beam treatment system related to the present embodiment can have either one or both of a configuration of preparation for addition coping with addition of the new facility and a configuration of preparation for replacement coping with replacement of a part of the existing facility.

First Embodiment

Figure 1:
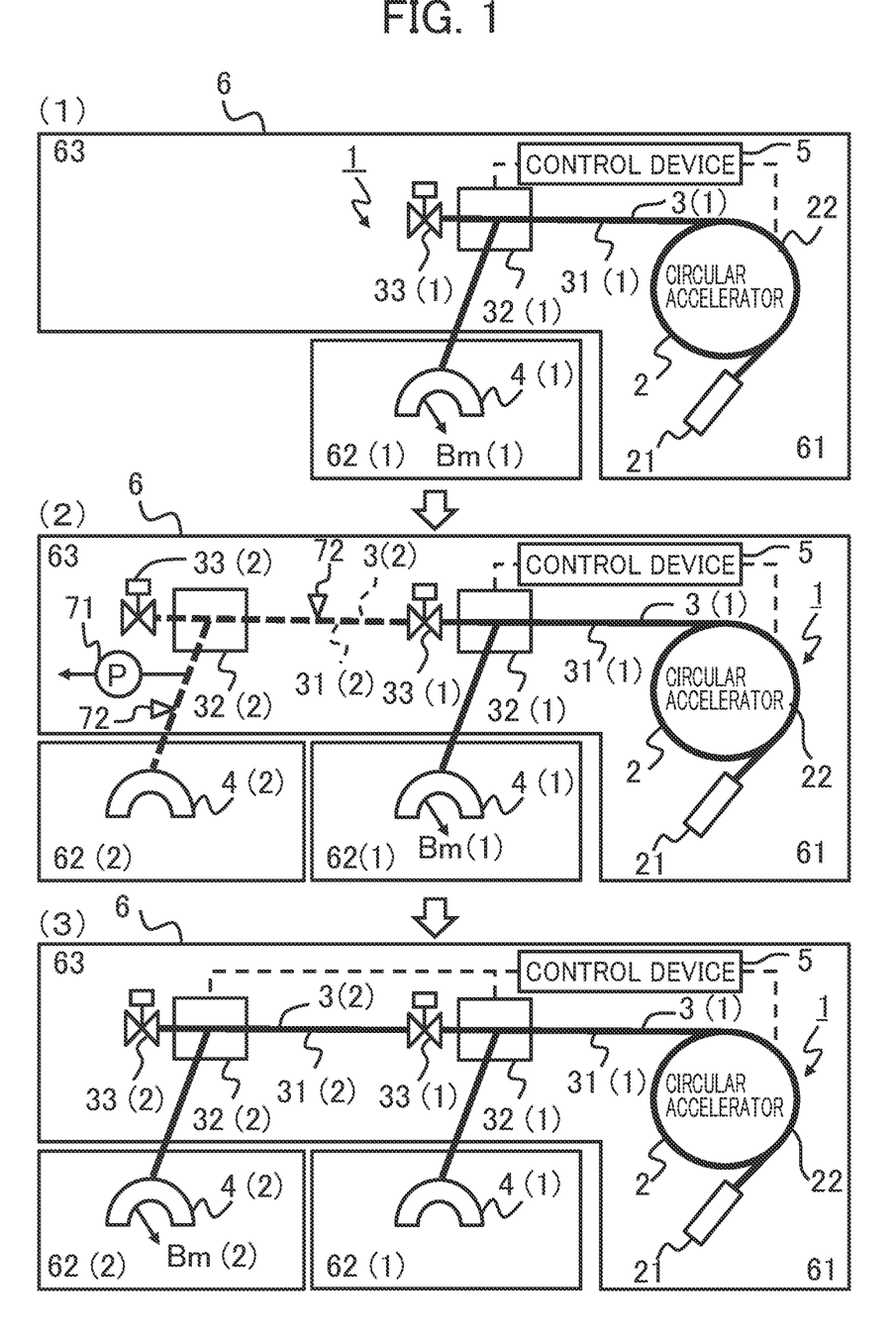
FIG. 1 is an explanatory drawing of a particle beam treatment system related to an embodiment.

The first embodiment will be explained using FIG. 1-FIG. 5. FIG. 1 is an explanatory drawing of a case where a new facility is added to a particle beam treatment system 1.

FIG. 1 (1) shows a configuration before adding the new facility. The particle beam treatment system 1 includes, for example, a charged particle beam generation device 2, a beam transportation device 3(1), an irradiation device 4(1), a control device 5, and a power supply device that is not illustrated.

The particle beam treatment system 1 is arranged in a building 6 such as an exclusive treatment ward of a hospital. In the building 6, an accelerator chamber 61, a treatment chamber 62(1), and a beam transportation chamber 63 for example are provided.

The charged particle beam generation device 2 is a device that generates a charged particle beam of protons, heavy ions and the like. The charged particle beam generation device 2 is installed in the accelerator chamber 61. The charged particle beam generation device 2 includes an ion source (not illustrated), a former accelerator 21, and a circular accelerator 22 for example. The circular accelerator 22 may be a synchrotron or may be a cyclotron. The ion source not illustrated is connected to the upstream side of the former accelerator 21, and the circular accelerator 22 is connected to the downstream side of the former accelerator 21.

The beam transportation device 3(1) is an example of "the first beam transportation device". The beam transportation device 3(1) is arranged in the beam transportation chamber 63. The beam transportation device 3(1) is connected to the downstream side of the charged particle beam generation device 2, and connects the charged particle beam generation device 2 and the irradiation device 4(1) to each other.

A charged particle beam generated by the charged particle beam generation device 2 passes through the beam transportation device 3(1), and is sent to the irradiation device 4(1) installed in the treatment chamber 62(1). The charged particle beam is irradiated by the irradiation device 4(1) to a diseased part of a patient as "a predetermined irradiation target". The irradiation device 4(1) is an example of "the first irradiation device". In FIG. 1, a beam irradiated by the irradiation device 4(1) is marked with a reference sign Bm(1).

The beam transportation device 3(1) includes, for example, a vacuum pipe line 31(1) and a deviation electromagnet 32(1) that is arranged in the vacuum pipe line 31(1). In the vacuum pipe line 31(1), a quadrupole electromagnet, a steering electromagnet, and a profile monitor for example (all of them are not illustrated) are arranged in addition to the deviation electromagnet 32(1).

The deviation electromagnet 32(1) that is an example of "the first branching device" is arranged in the middle of the vacuum pipe line 31(1). The deviation electromagnet 32(1) controls the direction of the charged particle beam according to a control signal from the control device 5, the charged particle beam passing through the vacuum pipe line 31(1).

The deviation electromagnet 32(1) includes one inlet where the charged particle beam enters, and plural outlets (2 outlets for example) from which the charged particle beam is emitted. The charged particle beam entering the deviation electromagnet 32(1) is emitted from any one of the plural outlets which are directed to different directions. One outlet is an outlet directed to the irradiation device 4(1). This outlet is an example of "the first irradiation device side outlet". Another outlet is an outlet directed to a second irradiation device 4(2). This outlet is an example of "the second irradiation device side outlet".

A vacuum valve 33(1) that is an example of "the first vacuum valve" is arranged beforehand in the middle of the beam transportation device 3(1). The vacuum valve 33(1) can be arranged on the outlet side of the deviation electromagnet 32(1). For example, the vacuum valve 33(1) can be arranged at the second irradiation device side outlet out of respective outlets of the deviation electromagnet 32(1). The vacuum valve 33(1) is in the normally closed state. Thereby, vacuum inside the beam transportation device 3(1) is kept.

The control device 5 is a device that controls the operation of the particle beam treatment system 1. The control device 5 controls the particle beam treatment system 1 according to the operation from a computer terminal not shown in the drawing. FIG. 1 illustrates as if the control device 5 is electrically connected only to the circular accelerator 22 and the deviation electromagnet 32(1). However, in fact, the control device 5 is connected to each part required for controlling the particle beam treatment system 1.

FIG. 1 (2) shows a case where the new facility (the second irradiation device 4(2) and the like) is added to the existing facility of the particle beam treatment system 1. In the beam transportation chamber 63, a beam transportation device 3(2) that is an example of "the second beam transportation device" is connected to the vacuum valve 33(1) that is in the closed state. In a treatment chamber 62(2) that should be called the second treatment chamber, the new irradiation device 4(2) is installed.

To the ultimate end (the ultimate end in the flow direction of the charged particle beam) of the beam transportation device 3(2), the new irradiation device 4(2) inside the treatment chamber 62(2) is connected. Thereby, the beam transportation device 3(2) allows the route from the vacuum valve 33(1) to the new irradiation device 4(2) to communicate. Because the vacuum valve 33(1) is closed, at the time point of FIG. 1 (2), the beam transportation device 3(2) and the beam transportation device 3(1) do not communicate to each other. That is to say, vacuum of the beam transportation device 3(1) which is the existing facility other than the adding object is kept.

In the middle of the beam transportation device 3(2), a deviation electromagnet 32(2) that is an example of "the second branching device" is arranged. The deviation electromagnet 32(2) controls the charged particle beam so as to head to the irradiation device 4(2) by a control signal from the control device 5.

Similarly to the description on the deviation electromagnet 32(1), in the deviation electromagnet 32(2), a vacuum valve 32(2) that is an example of "the second vacuum valve" is arranged. To be more specific, the vacuum valve 32(2) is arranged at an outlet other than the outlet directed to the irradiation device 4(2) out of 2 outlets included in the deviation electromagnet 32(2). This vacuum valve 32(2) is closed.

In the middle of the beam transportation device 3(2), a vacuum pump 71 and a pressure sensor 72 are arranged. The vacuum pump 71 sucks and discharges gas inside the beam transportation device 3(2) until the degree of vacuum detected by the pressure sensor 72 agrees to the degree of vacuum set to the beam transportation device 3(1). When the degree of vacuum (pressure) of the beam transportation device 3(1) and the degree of vacuum (pressure) of the beam transportation device 3(2) agree to each other, the vacuum valve 33(1) is opened.

FIG. 1 (3) shows a case where addition of the new facility to the particle beam treatment system 1 has been completed. When electrical construction has been completed and the irradiation device 4(2), the deviation electromagnet 32(2), and the like come to be under control of the control device 5, the conduction test, the final adjustment, and the like of the charged particle beam are executed. Thereby, the construction for addition of the new facility is completed, and a charged particle beam Bm(2) supplied from the charged particle beam generation device 2 to the irradiation device 4(2) is irradiated toward a diseased part.

Figure 2:
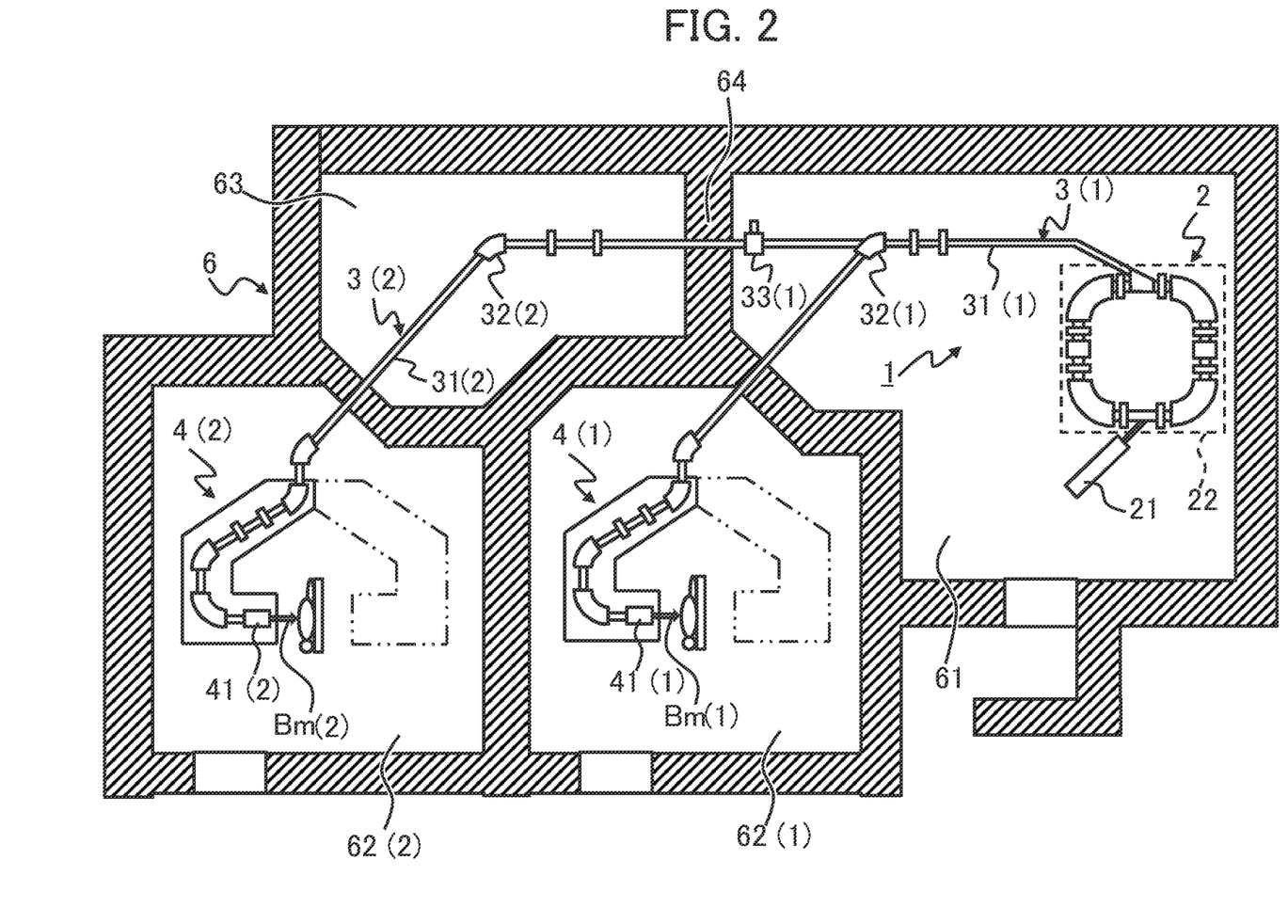
FIG. 2 is an explanatory drawing of a configuration of the particle beam treatment system.

FIG. 2 is a plan view that shows a configuration of the particle beam treatment system 1. The building 6 will be described in detail. A shielding wall 64 is arranged between the accelerator chamber 61 and the beam transportation chamber 63. The beam transportation device 3(2) and the beam transportation device 3(1) are connected to each other while penetrating the shielding wall 64. The beam transportation device 3(2) and the beam transportation device 3(1) can be separated or communicated each other by the vacuum valve 33(1).

The vacuum valve 33(1) is arranged inside the accelerator chamber 61 so as to be positioned on the front side of the shielding wall 64 for example. By arranging the vacuum valve 33(1) in front of the shielding wall 64, it is allowed that the construction and the like can be executed without receiving the impact by the accelerator 22 on the beam transportation chamber 63 side.

Figure 3:
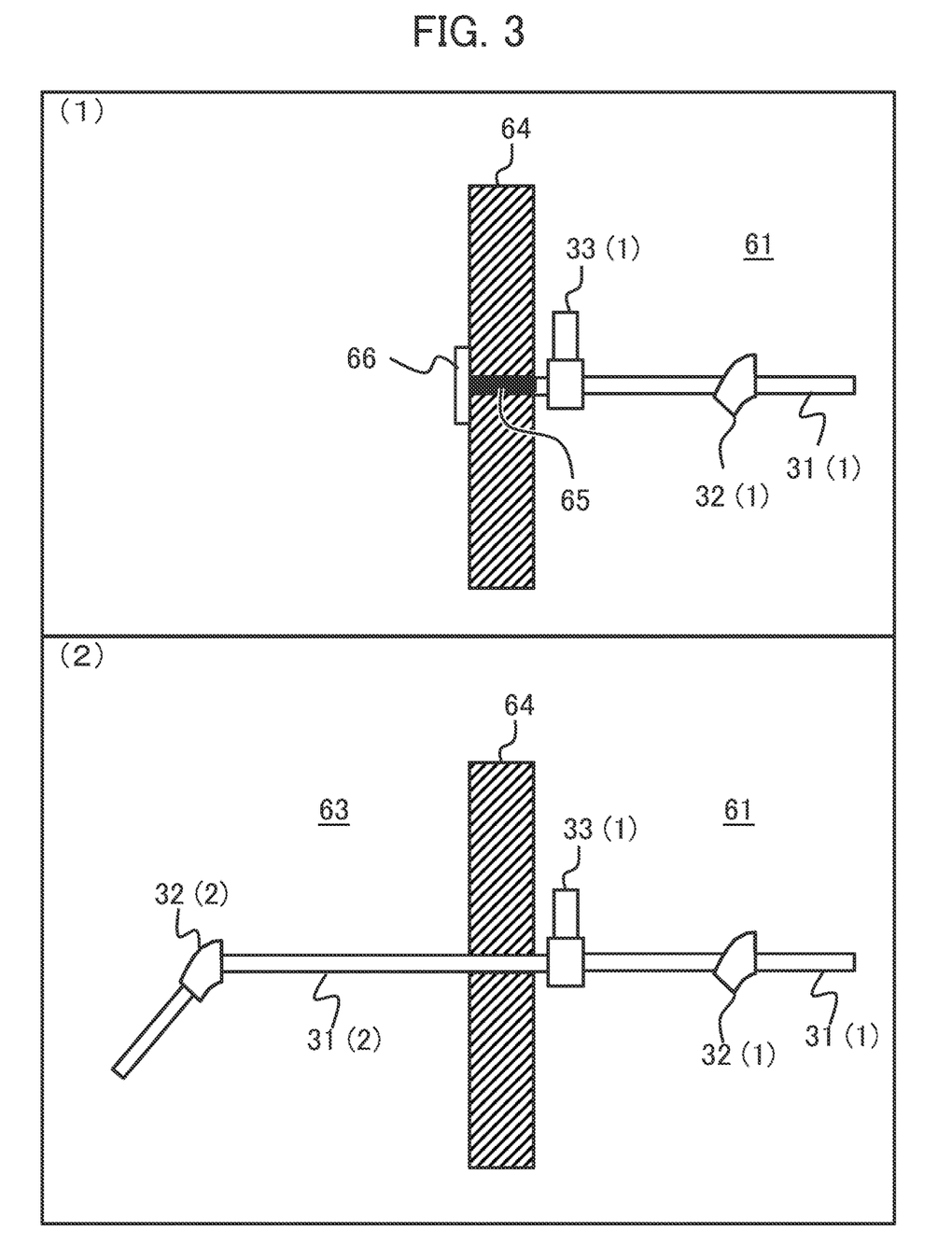
FIG. 3 is an explanatory drawing showing the relation of a beam transportation device, a shielding wall, and a vacuum valve, (1) shows a state before the extension construction, and (2) shows a state after the extension construction.

FIG. 3 is a cross-sectional view that shows the relation of the shielding wall 64 and the vacuum valve 33(1) and the like. FIG. 3 (1) shows a state before the construction for addition of the new facility namely a state of the time of delivering the existing facility. The end on the downstream side of the beam transportation device 3(1) is arranged so as to penetrate the shielding wall 64. The downstream side opening part of the beam transportation device 3(1) is capped by a flange 66. With respect to the beam transportation device 3(1), a shielding object 65 fills the range from the downstream side opening part of the beam transportation device 3(1) to the outlet of the vacuum valve 33(1). The shielding object 65 is configured as spherical bodies made of iron and steel for example. Thereby, it is prevented that the impact of the accelerator chamber 61 side reaches the beam transportation chamber 63 side before adding the new facility.

As shown in FIG. 3 (2), in the construction for addition of the new facility, after removing the flange 66 and the shielding object 65, the beam transportation device 3(2) and the beam transportation device 3(1) are connected to each other through the vacuum valve 33(1).

Figure 4:
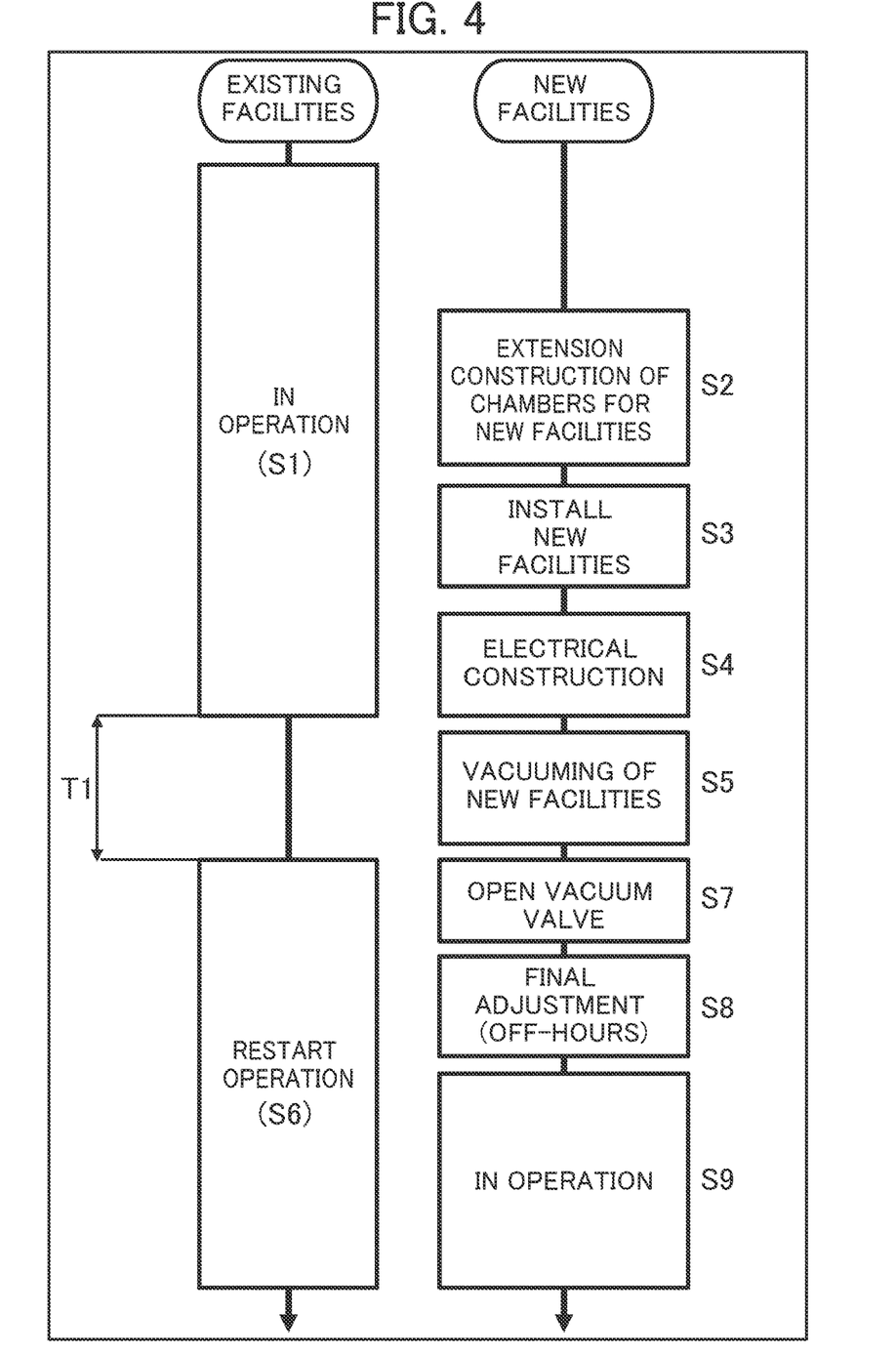
FIG. 4 is an explanatory drawing showing a general step of a case where new facilities are added.
Figure 5:
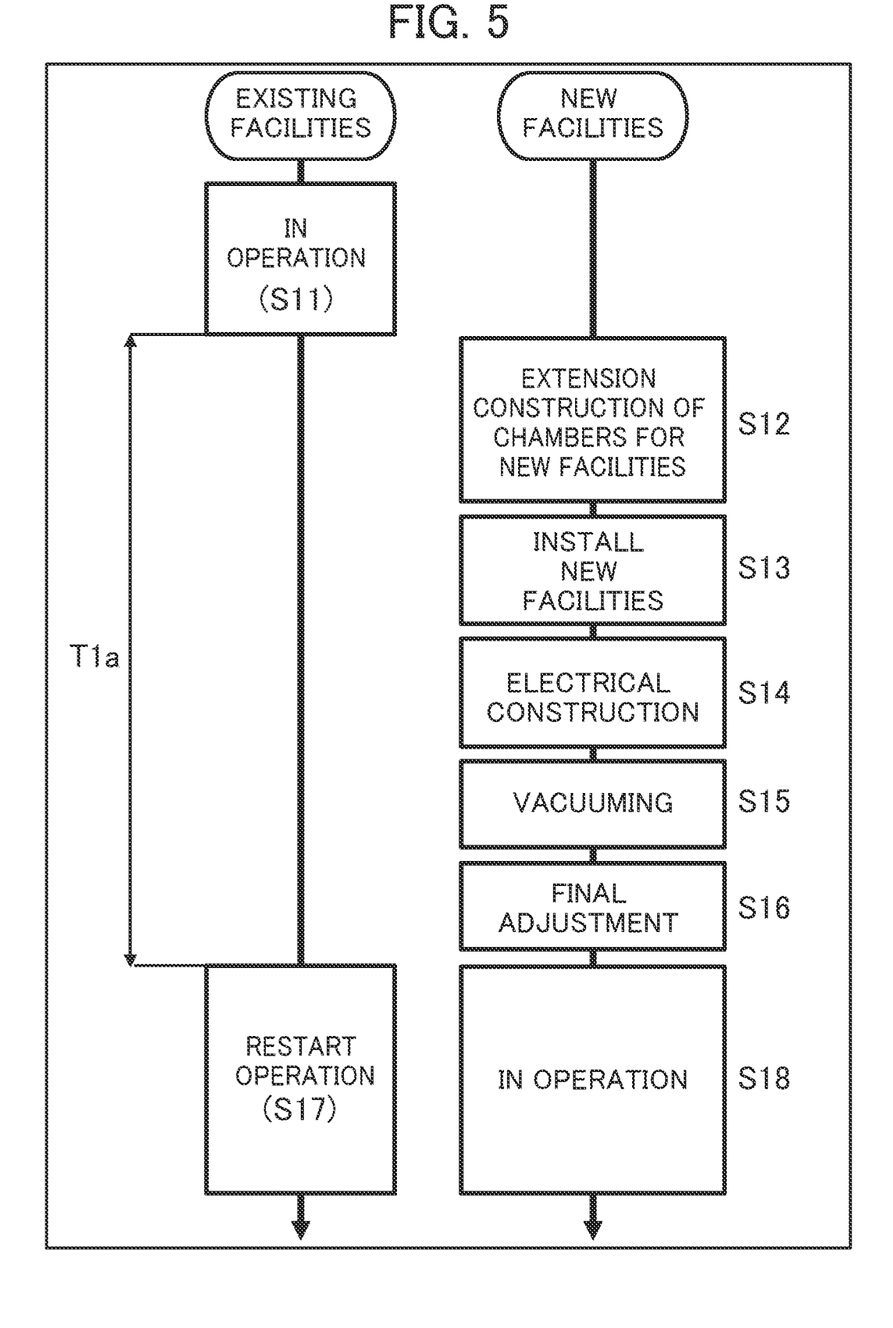
FIG. 5 is an explanatory drawing showing a general step as a comparative example to which the present embodiment is not applied.

FIG. 4 shows a flow of the steps required for the construction for addition of the new facility according to the present embodiment. In FIG. 4 and FIG. 5 described below, the outline of the main steps out of each step required for the construction is shown.

As described above, the existing facility is a configuration of a portion not becoming an object for addition or replacement of the facility out of the particle beam treatment system 1. An event that the existing facility is in operation means that treatment using the existing irradiation device 4(1) can be executed.

Before starting the construction for addition of the new facility, the vacuum valve 33(1) is closed. Therefore, because vacuum of the new facility side (the charged particle beam generation device 2, the beam transportation device 3(1), and the irradiation device 4(1)) is kept, the new facility can continue the operation in the same manner as before (S1).

During operation of the existing facility, the building construction for installing the irradiation device 4(2) and the beam transportation device 3(2) which are the new facilities is executed (S2). Also, anticipating expansion of the facility in the future, the treatment chamber 62(2) and the beam transportation chamber 63 may be built beforehand in the building 6.

When construction of the chambers is completed, the irradiation device 4(2) and the beam transportation device 3(2) are delivered and installed (S3). To be more specific, the irradiation device 4(2) is installed in the treatment chamber 62(2), and the beam transportation device 3(2) is installed in the beam transportation chamber 63.

Also, the electrical construction of the new facility is executed (S4). In the electrical construction, for example, the irradiation device 4(2) and the power supply are connected to each other, the deviation electromagnet 32(2) and the like of the beam transportation device 3(2) and the power supply are connected to each other, and the power supply of them and the control device 5 are connected to each other.

By activating the vacuum pump 71 in a state the vacuum valve 33(1) is kept closed after completion of the electrical construction, the pressure of the charged particle beam route (vacuum pipe line) included in the beam transportation device 3(2) and the irradiation device 4(2) is lowered to a predetermined pressure (S5). The predetermined pressure means the degree of vacuum required for transportation of the charged particle beam.

When the vacuuming work is completed, operation of the existing facility can be restarted (S6). Treatment using the existing irradiation device 4(1) can be restarted before completion of the final adjustment of the new irradiation device 4(2).

On the other hand, when vacuuming of the new facility is completed, the vacuum valve 33(1) is opened, and the beam transportation device 3(1) and the beam transportation device 3(2) communicate with each other (S7). Also, the final adjustment of the new facility namely the final adjustment of the irradiation device 4(2) is executed.

However, because operation of the existing irradiation device 4(1) has been restarted, the final adjustment of the irradiation device 4(2) having been added is executed in the period of time such as the night time, holiday, and the like for example (S8). In the final adjustment, the position, size, and the like of the charged particle beam supplied from the charged particle beam generation device 2 to the irradiation device 4(2) are adjusted for example. After completion of the final adjustment of the irradiation device 4(2), the irradiation device 4(2) also becomes operable (S9).

According to the present embodiment configured thus, the vacuum valve 33(1) is arranged beforehand on the boundary of the facility of the renewal object and the facility continuing to be used as it is, and the renewal object facility and the existing facility can be separated. Thereby, construction for addition of the new facility can be executed while keeping the degree of vacuum of the existing facility and running (operating) the existing facility, and the stop time of the existing facility can be shortened.

In an example of FIG. 4, a stop time T1 of the existing facility is generally equal to the time required for the electrical construction of the new facility (cable connection to the panel). On the other hand, FIG. 5 is a schematic drawing of the steps in a comparative example of a case where the present embodiment is not applied.

Because the comparative example does not include the vacuum valve 33(1) that separately manages the existing facility and the renewal object facility, the impact of the construction for the new facility is exerted to the existing facility also as it is. During the period of executing the construction for addition of the new facility, the existing facility cannot be operated. That is to say, during each step of the extension construction of the chamber for the new facility (S12), the installation construction of the new facility (S13), the electrical construction (S14), the vacuuming work so that the pressure of the new facility and the existing facility becomes a predetermined pressure (predetermined degree of vacuum) (S15), and the final adjustment work (S16) for example, treatment using the existing facility cannot be executed. Therefore, in the case of the comparative example, a stop time T1$a$ of the existing facility is longer than the stop time T1 of the particle beam treatment system 1 related to the present embodiment (T1$a$>T1).

According to the present embodiment, when the new facility is added, the stop time of the existing facility can be shortened, and the new facility can be added while continuing the treatment by the existing facility. Thereby, the capacity of the particle beam treatment system 1 can be expanded while securing the income, and the profit lowering risk in managing the business reduces.

Second Embodiment

The second embodiment will be explained using FIG. 6. Because respective embodiments described below including the present embodiment correspond to modifications of the first embodiment, explanation will be made focusing the difference against the first embodiment. In the present embodiment, by attaching the vacuum valve 33(2) beforehand also to the irradiation device 4(2) newly added, further expandability is secured.

Figure 6:
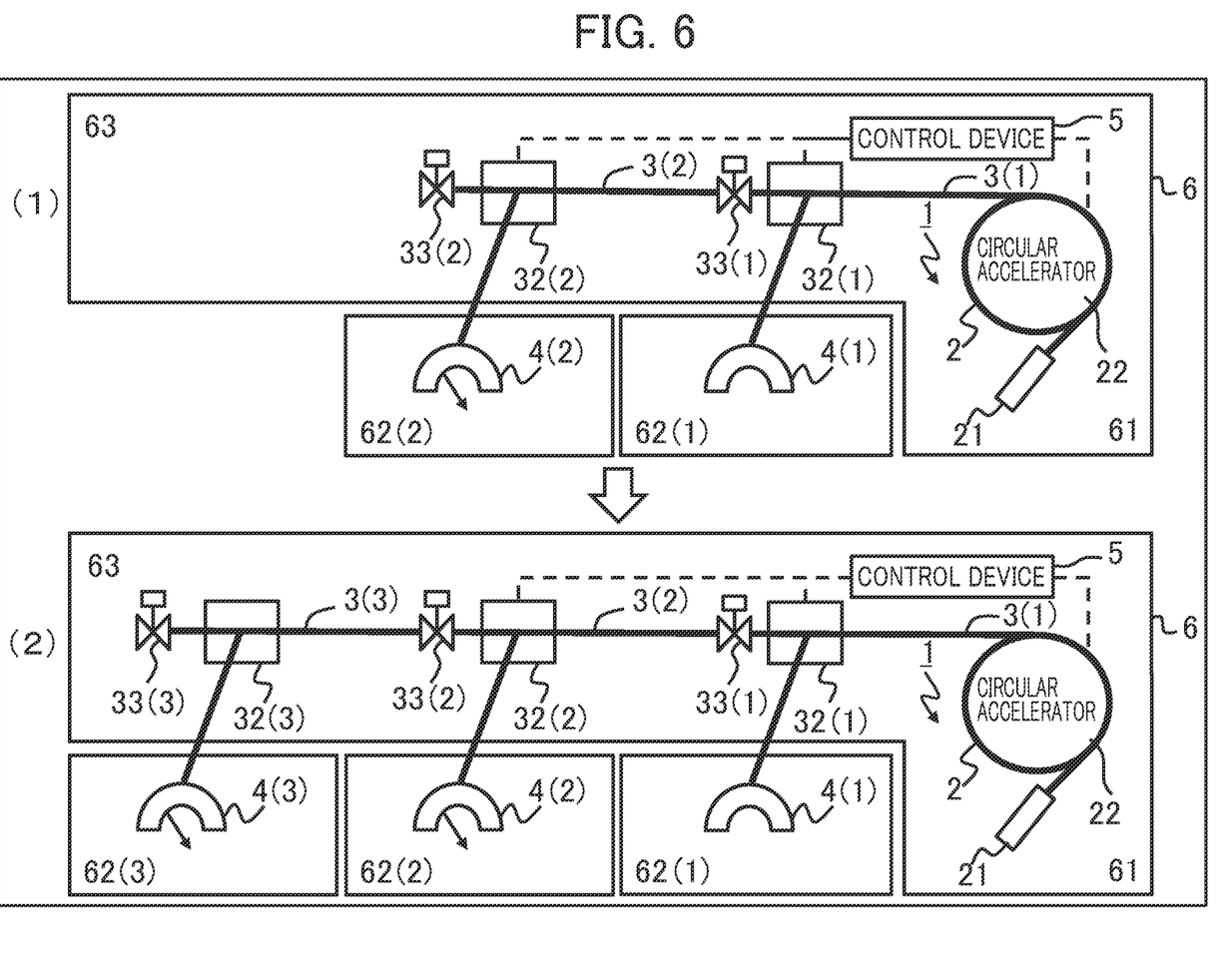
FIG. 6 is an explanatory drawing of a particle beam treatment system related to a second embodiment and is configured that the second irradiation device can be added.

FIG. 6 (1) shows a state that addition of the second irradiation device 4(2) has been completed. The vacuum valve 33(2) is arranged beforehand also in the beam transportation device 3(2) that is connected to the second irradiation device 4(2). Because the detailed attaching example of the vacuum valve 33(2) is similar to that of the vacuum valve 33(1) described in the first embodiment, explanation here will be omitted.

FIG. 6 (2) shows a state that a third irradiation device 4(3) has been further added. The method for connecting the third irradiation device 4(3) to the beam transportation device 3(2) through the vacuum valve 33(2) is similar to the method for connecting the second irradiation device 4(2) to the beam transportation device 3(1) through the vacuum valve 33(1). In FIG. 6, such case was described that 2 new devices 4(1), 4(2) were added to the initial configuration (the irradiation device 4(1), the charged particle beam generation device 2, and the beam transportation device 3(1)). The present invention is not limited to it, and 4 sets or more of new devices may be added.

Third Embodiment

Figure 7:
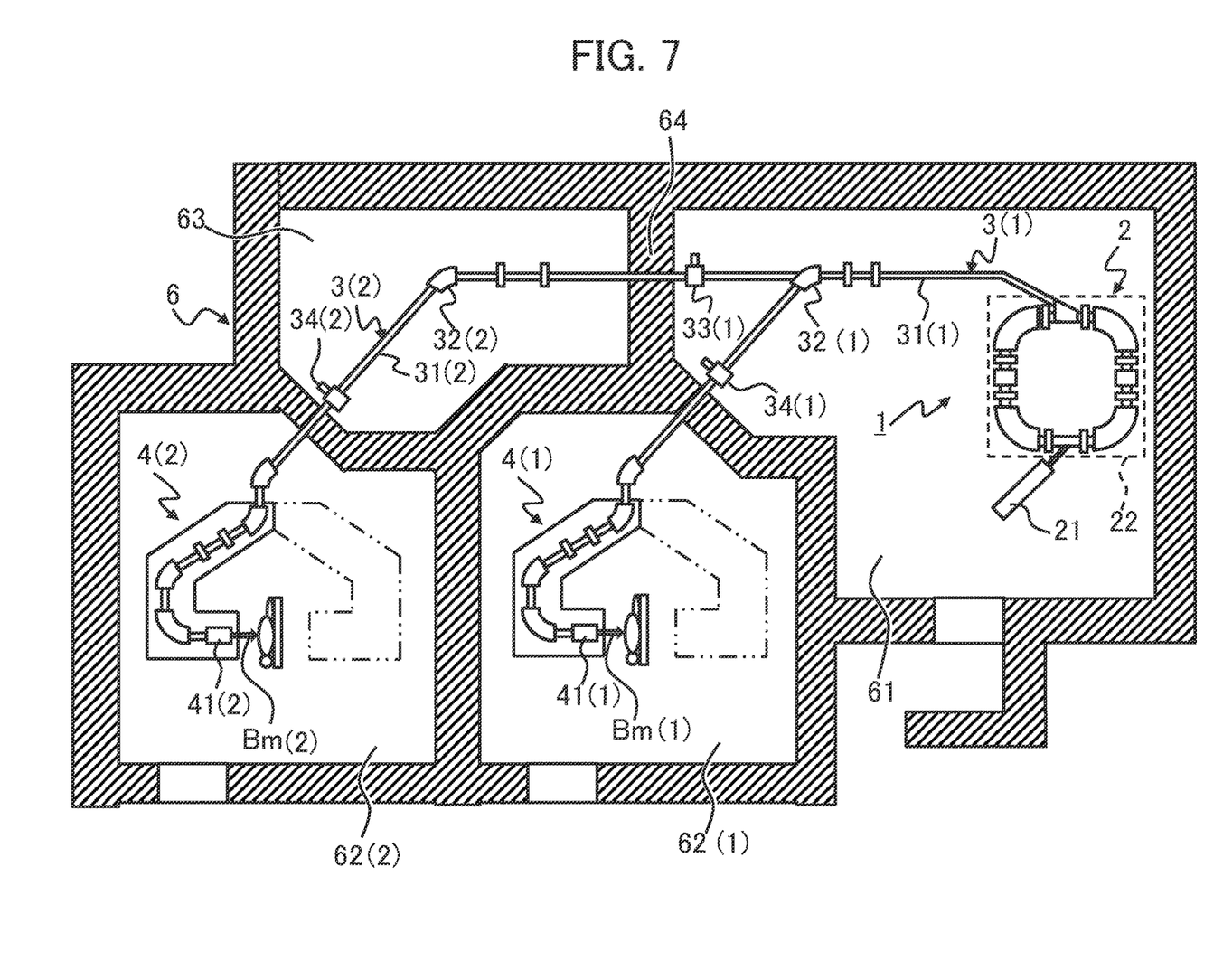
FIG. 7 is an explanatory drawing of a particle beam treatment system that is related to a third embodiment and shows a case where vacuum valves are arranged respectively at respective outlets included in a deflection device.

The third embodiment will be explained using FIG. 7. In the present embodiment, a case of not only adding the new facility to the existing facility but also replacing a part of the existing facility will be explained.

In the present embodiment, as described in FIG. 6, vacuum valves 33(2), 33(3) are arranged beforehand also in the new facility added. Further, in the present embodiment, in the beam transportation devices 3(1), 3(2) between the irradiation devices 4(1), 4(2) and the deviation electromagnets 32(1), 32(2), vacuum valves 34(1), 34(2) which are positioned on the front side of walls 67(1), 67(2) and are for replacing the facility are arranged respectively.

In the present embodiment configured thus, similarly to the first embodiment and the second embodiment, by using the vacuum valve 33(1) for adding the facility, the new irradiation device 4(2) can be added within a short period. Although it is omitted in FIG. 7, the vacuum valve 33(2) for adding the facility can be attached beforehand at the time of adding the new irradiation device 4(2).

Further, according to the present embodiment, because the vacuum valves 34(1), 34(2) for replacement are arranged beforehand in the irradiation devices 4(1), 4(2) also, replacement of the irradiation devices 4(1), 4(2) can be executed within a short period. For example, when the irradiation device 4(1) is to be replaced by another irradiation device, after closing the vacuum valve 34(1), the irradiation device 4(1) is detached, and the other irradiation device is attached. Also, using a vacuum pump not illustrated, the pressure inside the other irradiation device is made a predetermined degree of vacuum. By opening the vacuum valve 34(1) thereafter, the other irradiation device and the beam transportation device 3(1) can be connected to each other. The irradiation device 4(2) also can be replaced in a similar manner.

Fourth Embodiment

Figure 8:
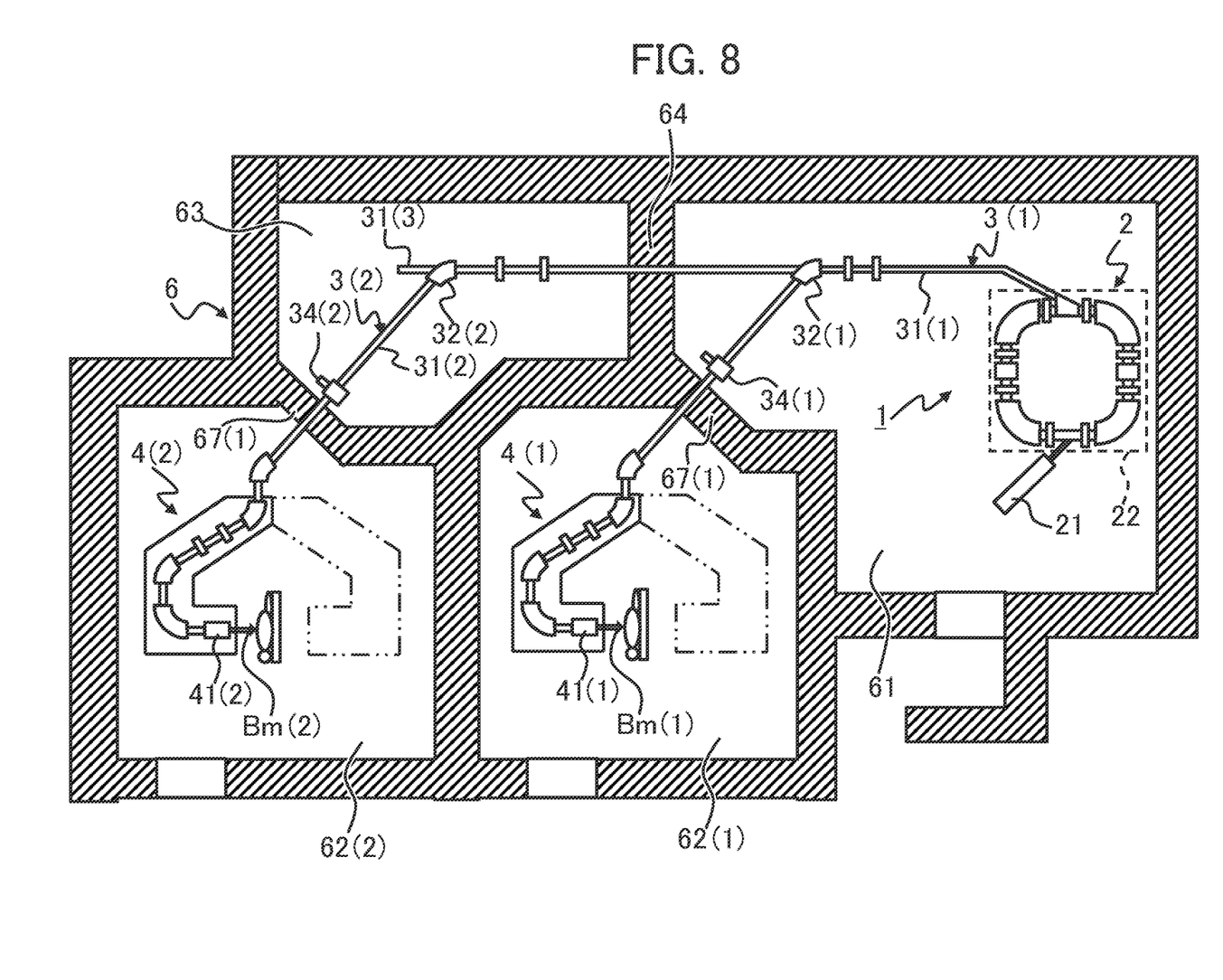
FIG. 8 is an explanatory drawing of a particle beam treatment system that is related to a fourth embodiment and shows a case where a vacuum valve is arranged for renewing the irradiation device.

The fourth embodiment will be explained using FIG. 8. In the present embodiment, the vacuum valve 33(1) for adding the facility is deleted from the configuration described in FIG. 7, and only the vacuum valves 34(1), 34(2) for replacing the facility are provided. In the present embodiment configured thus, the irradiation devices 4(1), 4(2) can be replaced within a short period.

Also, the present invention is not limited to the embodiments described above. A person with an ordinary skill in the art can execute various additions, alterations, and so on within the scope of the present invention. The embodiments described above are not limited to the configuration examples illustrated in the attached drawings. It is possible to appropriately change the configuration and the processing method of the embodiments within a scope for achieving the object of the present invention.

Also, respective configuration elements of the present invention can be sifted through optionally, and an invention including the sifted through configuration is also included in the present invention. Further, the configuration described in the claims can be combined other than the combinations explicitly shown in the claims.

LIST OF REFERENCE SIGNS

1: Particle beam treatment system
2: Charged particle beam generation device
3(1), 3(2), 3(3): Beam transportation device
4(1), 4(2), 4(3): Irradiation device
5: Control device
6: Building
21: Former accelerator
22: Circular accelerator
31(1), 31(2): Vacuum pipe line
32(1), 32(2): Deviation electromagnet
33(1), 33(2), 33(3): Vacuum valve
34(1), 34(2): Vacuum valve
61: Accelerator chamber
62(1), 62(2), 62(3): Treatment chamber
63: Beam transportation chamber

The invention claimed is:

1. A particle beam treatment system, comprising:
a charged particle beam generation device that generates a charged particle beam;
a first irradiation device that irradiates the charged particle beam to a predetermined irradiation target, the first irradiation device installed in a first treatment room where the charged particle beam is irradiated to a patient;
a first beam transportation device that transports the charged particle beam from the charged particle beam generation device to the first irradiation device;
a first vacuum valve that is arranged in a position of the first beam transportation device that is outside the first treatment room;
a first branching device that branches a destination of the charged particle beam is arranged in the first beam transportation device,
wherein the first irradiation device is connected at a connection point to the first branching device,
wherein an end portion, which includes an opening, of the first beam transportation device penetrates a shielding wall,
wherein the position of the first vacuum valve in the first beam transportation device is downstream from the connection point of the first irradiation device to the first branching device,
wherein a second beam transportation device that transports the charged particle beam to a second irradiation device is connected to the first branching device through the first vacuum valve,
wherein a second vacuum valve is arranged in the second beam transportation device,
wherein a second branching device that branches a destination of the charged particle beam is arranged in the second beam transportation device, and
the second vacuum valve is arranged at an outlet of the second branching device.

2. The particle beam treatment system according to claim 1,
wherein the first vacuum valve is arranged at an outlet of the first branching device.

3. The particle beam treatment system according to claim 1,
wherein the first branching device includes a first irradiation device side outlet that allows the charged particle beam to head to the first irradiation device and a second irradiation device side outlet that allows the charged particle beam to head to the second irradiation device, and
the first vacuum valve is arranged at the second irradiation device side outlet.

4. The particle beam treatment system according to claim 3,
wherein the first valve exists by a plurality,
a first vacuum valve that is one of the first valves of a plurality is arranged at the second irradiation device side outlet, and
a first vacuum valve that is another of the first valves of a plurality is arranged at the first irradiation device side outlet.

5. The particle beam treatment system according to claim 2,
wherein the first vacuum valve is arranged so as to be positioned between a shielding wall and the first branching device.

6. The particle beam treatment system according to claim 2,
wherein the first vacuum valve is arranged on a downstream side of the first branching device.

7. The particle beam treatment system according to claim 1,
  wherein the position of the first vacuum valve in the first beam transportation device is between the charged particle beam generation device and the shielding wall.

8. The particle beam treatment system according to claim 1,
  wherein the opening of the first transportation device is sealed.

9. The particle beam treatment system according to claim 1, further comprising:
  the second beam transportation device being connectable to the opening of the first transportation device,
  wherein after connecting the second beam transportation device to the opening of the first transportation device in a state that the first vacuum valve is closed, pressure on a route of the charged particle beam that passes through the second beam transportation device is lowered.

10. The particle beam treatment system according to claim 3,
  the second irradiation device side outlet is connected to the second irradiation device without a vacuum valve.

* * * * *